United States Patent
Wang et al.

(10) Patent No.: US 11,447,735 B2
(45) Date of Patent: Sep. 20, 2022

(54) ULTRASONIC CELLULAR STIMULATION DEVICE

(71) Applicant: National Taiwan University, Taipei (TW)

(72) Inventors: Jaw-Lin Wang, Taipei (TW); Ya-Cherng Chu, Taipei (TW)

(73) Assignee: National Taiwan University, Taipei (TW)

( * ) Notice: Subject to any disclaimer, the term of this patent is extended or adjusted under 35 U.S.C. 154(b) by 520 days.

(21) Appl. No.: 16/660,937

(22) Filed: Oct. 23, 2019

(65) Prior Publication Data

US 2020/0165560 A1    May 28, 2020

(30) Foreign Application Priority Data

Nov. 22, 2018 (TW) .................................. 107141677

(51) Int. Cl.
   *C12M 1/42*   (2006.01)
   *B06B 1/06*   (2006.01)

(52) U.S. Cl.
   CPC ............ *C12M 35/00* (2013.01); *C12M 35/04* (2013.01); *B06B 1/0625* (2013.01)

(58) Field of Classification Search
   CPC .............................. C12M 35/04; B06B 1/0625
   See application file for complete search history.

(56) References Cited

U.S. PATENT DOCUMENTS

| | | | | | |
|---|---|---|---|---|---|
| 3,200,369 | A | * | 8/1965 | Neubauer | B06B 1/0685 310/326 |
| 3,325,779 | A | * | 6/1967 | Supernaw | G10K 11/28 367/151 |
| 3,441,754 | A | * | 4/1969 | Heny | G10K 11/004 29/25.35 |
| 3,546,497 | A | * | 12/1970 | Craster | B06B 1/0666 367/160 |
| 3,555,311 | A | * | 1/1971 | Weber | B06B 1/0677 310/326 |
| 3,801,838 | A | * | 4/1974 | Kistler | G01L 9/008 310/338 |
| 4,173,725 | A | * | 11/1979 | Asai | B06B 1/0618 310/325 |
| 4,945,276 | A | * | 7/1990 | Mylvaganam | G01P 5/24 73/644 |

(Continued)

*Primary Examiner* — Jonathan M Hurst
(74) *Attorney, Agent, or Firm* — Amin, Turocy & Watson, LLP

(57) ABSTRACT

An ultrasonic cellular stimulation device includes: an ultrasonic transducer for generating a vibration wave; an upper cap having a fixing portion disposed on a lateral surface thereof; and a lower cap having a first surface and a second surface, and including: a recess indenting the first surface; an abutment portion located at a bottom of the recess; and an opening formed in the second surface and being in communication with the recess. The upper cap is partially received in the recess. The ultrasonic transducer is clamped and fixed between the fixing portion and the first surface. A glass piece is disposed on the abutment portion and fixed between the upper cap and the lower cap, such that the vibration wave is conveyed from the first surface into the abutment portion and the glass piece and a uniform and controllable sound field is generated above the glass piece.

10 Claims, 5 Drawing Sheets

(56) References Cited

U.S. PATENT DOCUMENTS

| | | | | |
|---|---|---|---|---|
| 5,452,267 A * | 9/1995 | Spevak | ............... | G10K 13/00 |
| | | | | 310/334 |
| 6,246,154 B1 * | 6/2001 | Gluszyk | ............... | G10K 11/004 |
| | | | | 310/334 |
| 6,719,449 B1 * | 4/2004 | Laugharn, Jr. | ...... | B01F 35/2115 |
| | | | | 366/127 |
| 6,881,314 B1 * | 4/2005 | Wang | ............... | B01J 19/0093 |
| | | | | 204/600 |
| 6,990,046 B2 * | 1/2006 | Gluszyk | ............... | G01F 23/2968 |
| | | | | 367/174 |
| 9,074,952 B2 * | 7/2015 | Pletscher | ............... | G01L 23/10 |
| 10,260,035 B2 * | 4/2019 | Choi | ............... | C12N 13/00 |
| 10,428,324 B1 * | 10/2019 | Coons | ............... | C12N 1/12 |
| 10,737,953 B2 * | 8/2020 | Lipkens | ............... | B06B 1/06 |
| 2004/0001809 A1 * | 1/2004 | Brisken | ............... | A61N 7/00 |
| | | | | 604/20 |
| 2004/0191906 A1 * | 9/2004 | Holzer | ............... | C12M 35/04 |
| | | | | 435/383 |
| 2006/0223185 A1 * | 10/2006 | Fedorov | ............... | C12M 35/04 |
| | | | | 435/461 |
| 2006/0236747 A1 * | 10/2006 | Greenleaf | ............... | A61H 23/0236 |
| | | | | 73/1.82 |
| 2014/0038257 A1 * | 2/2014 | Subramanian | ............... | A61N 7/00 |
| | | | | 435/289.1 |
| 2014/0154795 A1 * | 6/2014 | Lipkens | ............... | B01D 17/04 |
| | | | | 435/297.2 |
| 2015/0376664 A1 * | 12/2015 | Ghanati | ............... | C12P 17/02 |
| | | | | 435/29 |
| 2017/0107506 A1 * | 4/2017 | Boer | ............... | C12M 41/12 |
| 2017/0166860 A1 * | 6/2017 | Presz, Jr. | ............... | B06B 1/06 |
| 2017/0218323 A1 * | 8/2017 | Lipkens | ............... | C12M 29/18 |
| 2018/0239007 A1 * | 8/2018 | Sugae | ............... | H04R 1/40 |
| 2020/0038914 A1 * | 2/2020 | Fujimoto | ............... | B06B 1/0625 |
| 2021/0310913 A1 * | 10/2021 | Lahoud | ............... | C12M 35/04 |

* cited by examiner

ULTRASONIC CELLULAR STIMULATION DEVICE

BACKGROUND

1. Technical Field

The present disclosure relates to ultrasonic cellular stimulation devices, and, more particularly, to a ultrasonic cellular stimulation device that stimulates cells with ultrasound and observes cell response in real time.

2. Description of the Prior Art

Ultrasonic techniques are widely applied to a variety of medical fields, such as diagnosing, and healing bone fracture or soft-tissue. People now pay their attention on the interaction of low intensity pulsed ultrasound (LIPUS) with tissues and cells. Research results show that the LIPUS has a significant bioeffect on the tissues and cells.

However, results obtained by existing LIPUS devices cannot be reproduced reliably due to in vitro experimental conditions. The actual strength of a ultrasonic wave applied to the tissues and cells is different from the measured strength of the ultrasonic wave because the ultrasonic wave is affected by multiple reflective and standing waves and the spacious energy distribution of a transducer. Therefore, scientists cannot rely on the existing LIPUS devices to validate cellular responses to ultrasound stimulation repeatedly.

Therefore, how to solve the problem of the prior art is becoming an urgent issue in the art.

SUMMARY

In view of the above drawbacks of the prior art, the present disclosure provides an ultrasonic cellular stimulation device, comprising: at least one ultrasonic transducer configured for generating a vibration wave; and a lower cap having a first surface and a second surface corresponding to the first surface, and comprising: a recess indenting the first surface of the lower cap; an abutment portion located at a bottom of the recess; and an opening formed in the second surface of the lower cap, the opening being in communication with the recess and having a diameter less than a diameter of the recess, wherein the at least one ultrasonic transducer is disposed on the first surface around the recess of the lower cap, such that the vibration wave is conveyed from the first surface of the lower cap into the abutment portion.

In an embodiment, the ultrasonic cellular stimulation device further comprises an upper cap partially received in the recess of the lower cap and having at least one fixing portion on a lateral surface thereof.

In an embodiment, the at least one fixing portion of the upper cap is configured for clamping and fixing the at least one ultrasonic transducer between the at least one fixing portion and the first surface around the recess of the lower cap.

In an embodiment, the ultrasonic cellular stimulation device further comprises a glass piece disposed on the abutment portion in the recess of the lower cap, and a uniform and controllable sound field is formed on the glass piece when the vibration wave is conveyed into the abutment portion.

In an embodiment, a reception portion is recessed into the abutment portion around the opening in the recess of the lower cap and configured for receiving the glass piece.

In an embodiment, the upper cap has a flange, and an O-ring coupled to an outer side of the flange fixes the glass piece to the reception portion when the upper cap is received in the recess of the lower cap.

In an embodiment, the glass piece is a round glass piece having a diameter ranging from 10 mm to 40 mm and a thickness ranging from 0.15 mm to 0.4 mm.

In an embodiment, the upper cap and the lower cap are made of a highly rigid material, such as white steel and stainless steel.

In an embodiment, the at least one ultrasonic transducer is adhered to the first surface of the lower cap.

The ultrasonic cellular stimulation device according to the present disclosure allows precise dose control for a low intensity pulsed ultrasound, and allows a user to observe cell changes in real time. In the ultrasonic cellular stimulation device according to the present disclosure, at least one ultrasonic transducer is clamped and fixed between the fixing portion of the upper cap and the first surface around the recess of the lower cap. The vibration wave generated by the ultrasonic transducer can be conveyed from the first surface of the lower cap into the abutment portion at the bottom of the recess of the lower cap, and the uniform and controllable sound field can thus be formed on the glass piece on the abutment portion. The ultrasonic cellular stimulation device according to the present disclosure can avoid any possible biocontamination.

DETAILED DESCRIPTION

The following illustrative embodiments are provided to illustrate the disclosure of the present disclosure, these and other advantages and effects can be apparently understood by those in the art after reading the disclosure of this specification. The present disclosure can also be performed or applied by other different embodiments. The details of the specification may be on the basis of different points and applications, and numerous modifications and variations can be devised without departing from the spirit of the present disclosure.

Figure 1A:
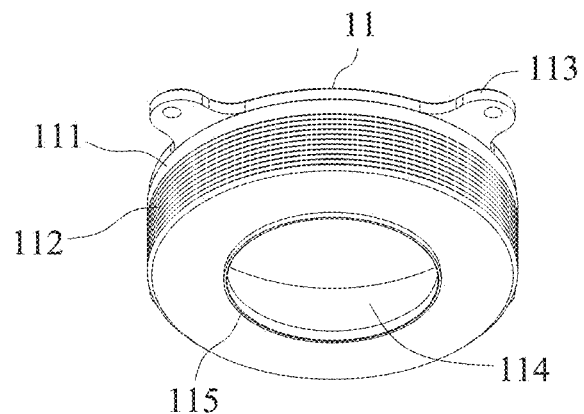
FIG. 1A is a bottom view of an upper cap of an ultrasonic cellular stimulation device according to the present disclosure.
Figure 1B:
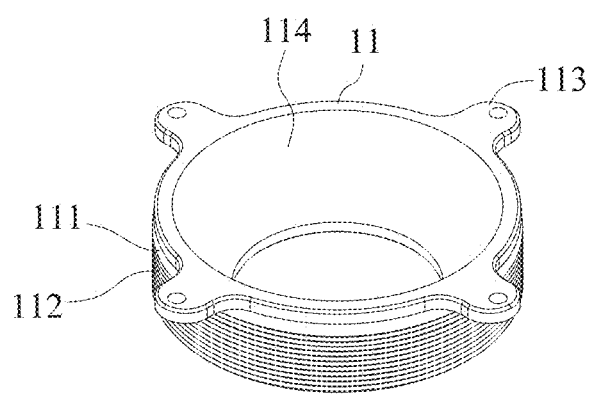
FIG. 1B is a top view of the upper cap of the ultrasonic cellular stimulation device according to the present disclosure.

FIG. 1A is a top view of an upper cap 11 of an ultrasonic cellular stimulation device 1 according to the present disclosure. FIG. 1B is a bottom view of the upper cap 11. The upper cap 11 is nearly cylindrical, and has at least one fixing portion 113 disposed on a lateral surface 111 thereof and an outer thread 112 on the lateral surface 111. The upper cap 11 also has a through hole 114 penetrating two surfaces thereof. A flange 115 is formed on a surface around the through hole 114 of a bottom portion of the upper cap 11.

Figure 2A:
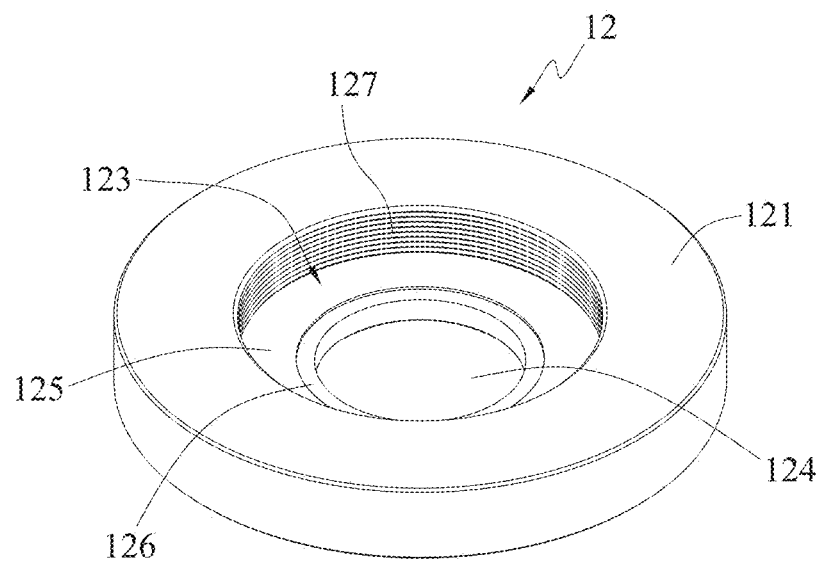
FIG. 2A is a bottom view of a lower cap of an ultrasonic cellular stimulation device according to the present disclosure.
Figure 2B:
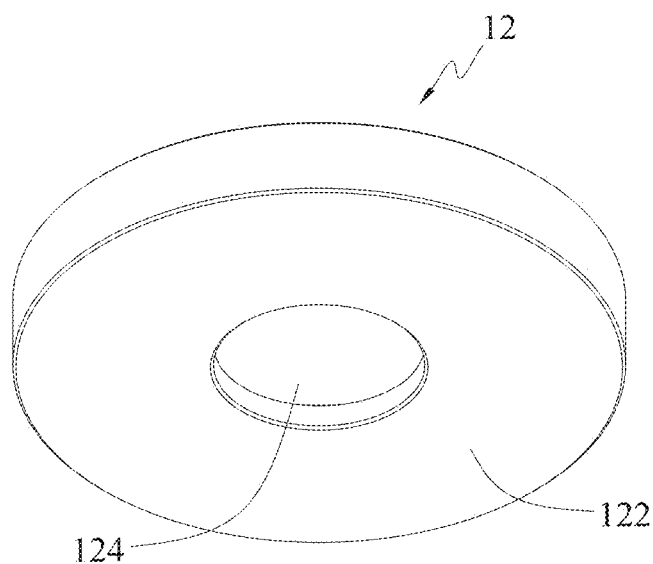
FIG. 2B is a top view of the lower cap of the ultrasonic cellular stimulation device according to the present disclosure.

FIG. 2A is a top view of a lower cap 12 of the ultrasonic cellular stimulation device 1 according to the present disclosure. FIG. 2B is a bottom view of the lower cap 12. The lower cap 12 is nearly cylindrical, and has a first surface 121 and a second surface 122 corresponding to the first surface 121. The lower cap 12 comprises a recess 123 and an opening 124. The recess 123 recesses inward from the first surface 121 of the lower cap 12. The opening 124 is formed in the second surface 122 of the lower cap 12 and in communication with the recess 123. The opening 124 has a diameter less than that of the recess 123. An abutment portion 125 is formed at a bottom of the recess 123. A reception portion 126 is recessed into the abutment portion 125 and located around the opening 124 in the recess 123 of the lower cap 12. An inner thread 127 is formed on a lateral wall of the recess 123 of the lower cap 12, and corresponds to the outer thread 112 formed on the lateral surface 111 of the upper cap 11.

Figure 3:
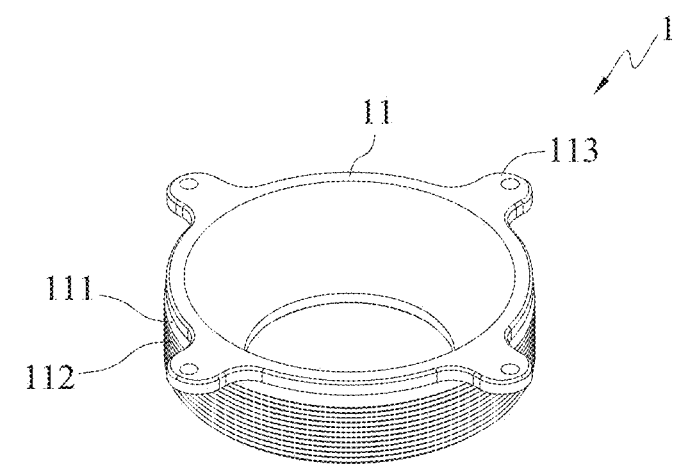
FIG. 3 is an exploded view of an ultrasonic cellular stimulation device according to the present disclosure.
Figure 3:
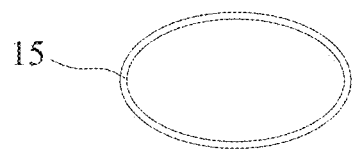
Figure 3:
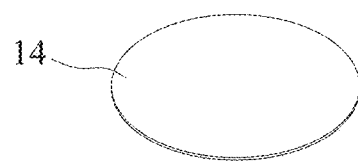
Figure 3:
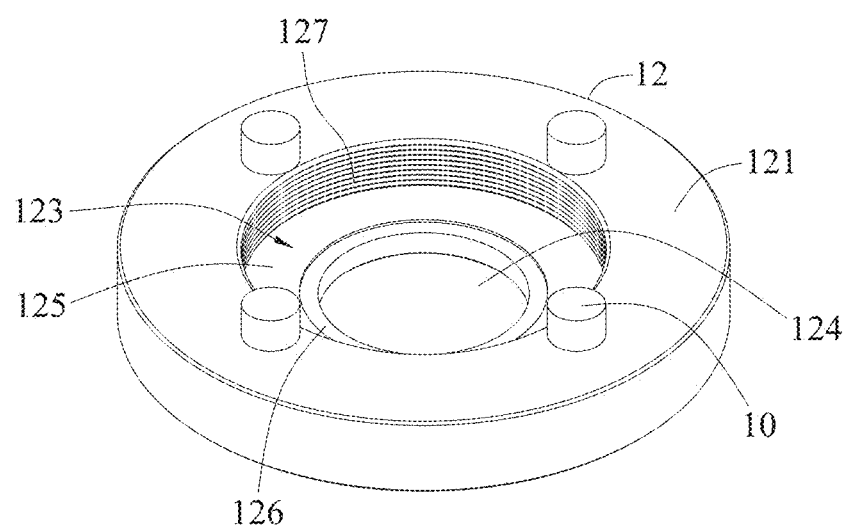

FIG. 3 is an exploded view of the ultrasonic cellular stimulation device 1 according to the present disclosure. The ultrasonic cellular stimulation device 1 comprises at least one ultrasonic transducer 10, the upper cap 11, the lower cap 12 and a glass piece 14. The ultrasonic transducer 10 generates a vibration wave. In an embodiment, the ultrasonic transducer 10 is a piezoelectric ceramic transducer (PZT). In another embodiment, the vibration wave has a frequency of 1 MHz to 3 MHz.

In an embodiment, the upper cap 11 is partially received in the recess of the lower cap 12, the outer thread 112 of the upper cap 11 is screwed to the inner thread 127 in the recess 123 of the lower cap 12, and the ultrasonic transducer 10 is clamped and fixed between the fixing portion 113 of the upper cap 11 and the first surface 121 around the recess 123 of the lower cap 12. The at least one ultrasonic transducer 10 may have different frequencies. In another embodiment, the upper cap 11 is a male connector, and the lower cap 12 is a female connector that can be mounted onto the male connector.

In an embodiment, the at least one ultrasonic transducer 10 has four ultrasonic transducers 10, and the upper cap 11 also has four fixing portions 113 correspondingly. These four ultrasonic transducers 10 are disposed on four corners on the first surface 121 of the lower cap 12 with respect to the recess 123, respectively. In an embodiment, the ultrasonic transducers 10 can be disposed in another manner. In another embodiment, the upper cap 11 does not have any fixing portion 113, and the ultrasonic transducer 10 is adhered to the first surface 121 of the lower cap 12, to address a scenario that the ultrasonic transducer 10 having a different frequency is replaced.

In an embodiment, the glass piece 14 is disposed on the abutment portion 125 in the recess 123 of the lower cap 12. In another embodiment, the glass piece 14 is received in the reception portion 126 recessed in the abutment portion 125. When the upper cap 11 is received in the recess 123 of the lower cap 12, the glass piece 14 is sandwiched between the flange 115 of the upper cap 11 and the reception portion 126 of the lower cap 12. The glass piece 14 provides high transmittancy required when cells are viewed by a microscope, and high rigidity required for a uniform sound field.

In another embodiment, the glass piece 14 is replaced with other highly rigid, highly hard thin piece.

In an embodiment, the ultrasonic cellular stimulation device 1 further comprises an O-ring 15 disposed on an outer side of the flange 115 of the upper cap 11, and acting as a buffer when the glass piece 14 is sandwiched between the flange 115 of the upper cap 11 and the reception portion 126 of the lower cap 12, so that the flange 115 of the upper cap 11 will not crash the glass piece 14. The O-ring 15 also acts as a seal that prevents moisture from permeating into the upper cap 11.

In an embodiment, the glass piece 14 is a round glass piece having a diameter of 40 mm and a thickness of 0.4 mm, and corresponds to a 35 mm cell culture dish. In an embodiment, the distance that the reception portion 126 recessed into the abutment portion 125 is approximately equal to the thickness of the glass piece 14. In another embodiment, the glass piece 14 is a round glass piece having a diameter of 90 mm and a thickness of 0.4 mm, and corresponds to a 90 mm cell culture dish. In yet another embodiment, the glass piece 14 is a round glass piece having a diameter ranging from 10 mm to 30 mm and a thickness of 0.15 mm for cells to be cultured thereon directly, with the cell culture dish omitted.

In an embodiment, the upper cap 11 and the lower cap 12 are made of white steel, stainless steel, or other highly rigid material suitable in a high temperature sterilization environment such that the cells, before being stimulated, will be sterilized, to avoid microbiosis.

Figure 4:
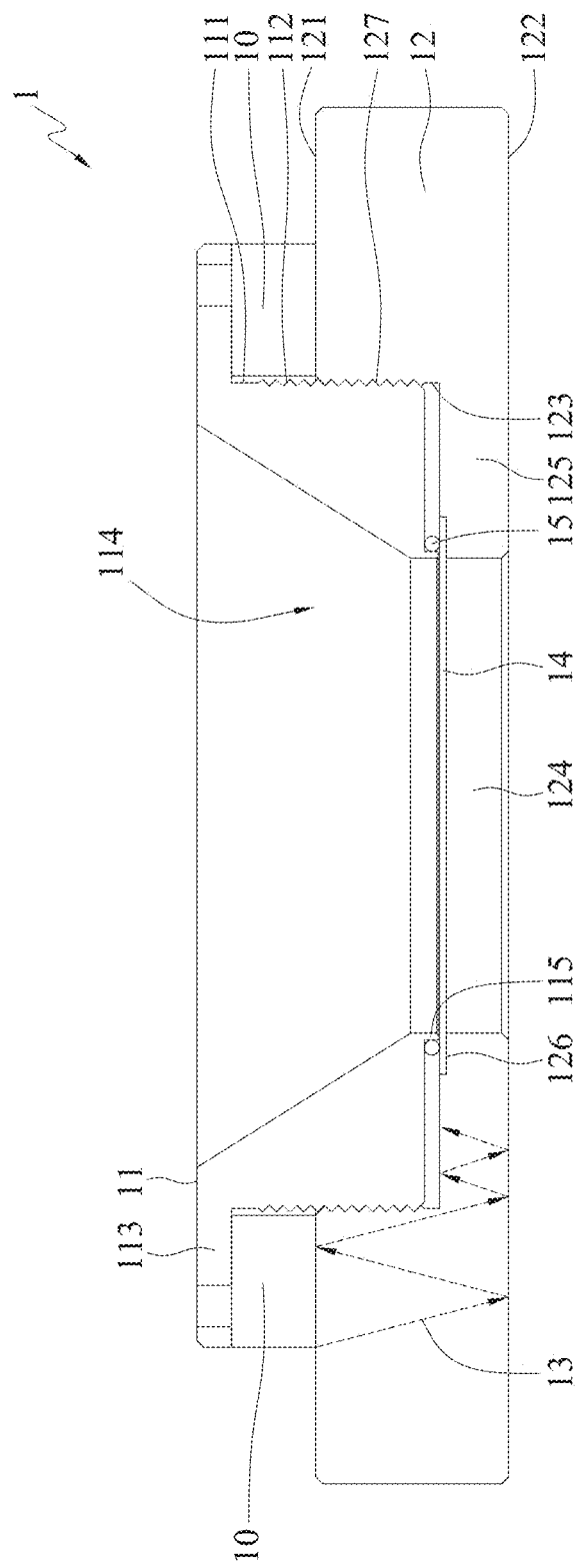
FIG. 4 is a cross-sectional view of an ultrasonic cellular stimulation device according to the present disclosure.
Figure 5:
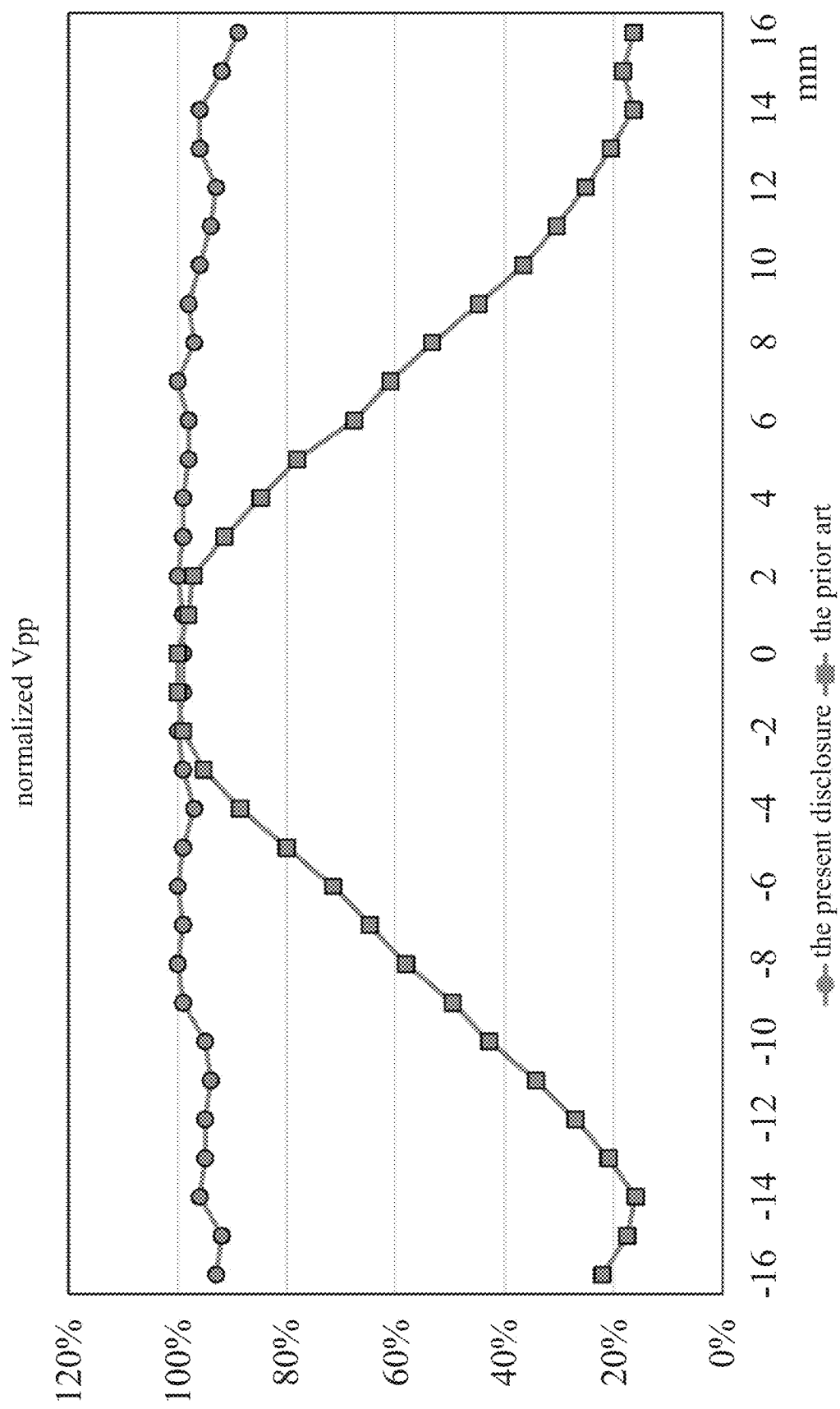
FIG. 5 is a graph showing the amplitudes measured on a glass piece of an ultrasonic cellular stimulation device according to the present disclosure and the prior art.

FIG. 4 is a cross-sectional view of the ultrasonic cellular stimulation device 1. When the upper cap 11 is received in the recess 123 of the lower cap 12 and clamps and fixes the glass piece 14, the ultrasonic transducer 10 may start to generate a vibration wave 13, which will be conveyed from the first surface 121 of the lower cap 12 (i.e., an incident radiation wave) into the abutment portion 125 and to the glass piece 14, such that a uniform and controllable sound field is formed on the glass piece 14 that can be controlled by the parameters such as frequency, amplitude or duty-cycle of the ultrasonic wave. The uniform and controllable sound field formed on the glass piece 14 can stimulate the cell in the cell culture dish above the glass piece 14. As shown in FIG. 5, which is an amplitude variation graph, compared with the prior art, the ultrasonic cellular stimulation device 1 according to the present disclosure has amplitudes measured at a central point (located at 0 mm) or other points (e.g., 12 mm away from the central point) in a radial direction that do not vary abruptly, but are stable, which indicates that the sound field in a chamber space on the glass piece 14 has uniform strength. Therefore, the cells cultured on the glass piece 14 are exposed to ultrasonic energy having constant amount over time.

In an embodiment, the ultrasonic cellular stimulation device 1 is mounted on a microscope in an experiment room, allowing a user to observe the cells cultured on the glass piece 14 through the through hole 114 of the upper cap 11.

In an ultrasonic cellular stimulation device according to the present disclosure, at least one ultrasonic transducer is clamped and fixed between a fixing portion of an upper cap and a first surface around a recess of a lower cap, a vibration wave generated by a ultrasonic transducer can be conveyed from the first surface of the lower cap into an abutment portion located at a bottom of the recess of the lower cap, and a uniform and controllable sound field can thus be formed on the glass piece on the abutment portion. Therefore, the ultrasonic cellular stimulation device according to the present disclosure allows precise exposure control for a low intensity pulsed ultrasound. The ultrasonic cellular stimulation device according to the present disclosure has a simple structure, is easy to be carried, can be mounted on a microscope in any experiment room, and can be sterilized before its use to avoid any possible biocontamination.

The foregoing descriptions of the detailed embodiments are only illustrated to disclose the features and functions of the present disclosure and not restrictive of the scope of the present disclosure. It should be understood to those in the art that all modifications and variations according to the spirit and principle in the disclosure of the present disclosure should fall within the scope of the appended claims.

What is claimed is:

1. An ultrasonic cellular stimulation device, comprising:
at least one ultrasonic transducer configured for generating a vibration wave; and
a lower cap having a first surface and a second surface corresponding to the first surface, and comprising:
a recess indenting the first surface of the lower cap;
an abutment portion located at a bottom of the recess; and
an opening formed in the second surface of the lower cap, the opening being in communication with the recess and having a diameter less than a diameter of the recess,
wherein the at least one ultrasonic transducer is disposed on the first surface around the recess of the lower cap, such that the vibration wave is conveyed from the first surface of the lower cap into the abutment portion.

2. The ultrasonic cellular stimulation device of claim 1, further comprising an upper cap partially received in the recess of the lower cap and having at least one fixing portion on a lateral surface thereof.

3. The ultrasonic cellular stimulation device of claim 2, wherein the at least one fixing portion of the upper cap is configured for clamping and fixing the at least one ultrasonic transducer between the at least one fixing portion and the first surface around the recess of the lower cap.

4. The ultrasonic cellular stimulation device of claim 2, further comprising a glass piece disposed on the abutment portion in the recess of the lower cap, wherein a uniform and controllable sound field is formed on the glass piece when the vibration wave is conveyed into the abutment portion.

5. The ultrasonic cellular stimulation device of claim 4, further comprising a reception portion concavely formed on the abutment portion around the opening in the recess of the lower cap and configured for receiving the glass piece.

6. The ultrasonic cellular stimulation device of claim 5, further comprising an O-ring, wherein the upper cap has a flange, and the O-ring is coupled to an outer side of the flange and fixes the glass piece to the reception portion when the upper cap is received in the recess of the lower cap.

7. The ultrasonic cellular stimulation device of claim 4, wherein the glass piece is a round glass piece having a diameter ranging from 10 mm to 40 mm and a thickness ranging from 0.15 mm to 0.4 mm.

8. The ultrasonic cellular stimulation device of claim 2, wherein the upper cap and the lower cap are made of a rigid material.

9. The ultrasonic cellular stimulation device of claim 8, wherein the rigid material is white steel or stainless steel.

10. The ultrasonic cellular stimulation device of claim 1, wherein the at least one ultrasonic transducer is adhered to the first surface of the lower cap.

* * * * *